United States Patent
Forster

(10) Patent No.: US 8,874,186 B2
(45) Date of Patent: Oct. 28, 2014

(54) APPARATUS AND METHOD FOR MONITORING PHYSIOLOGICAL PARAMETERS USING ELECTRICAL MEASUREMENTS

(75) Inventor: Ian J. Forster, Essex (GB)

(73) Assignee: Avery Dennison Corporation, Glendale, CA (US)

( * ) Notice: Subject to any disclaimer, the term of this patent is extended or adjusted under 35 U.S.C. 154(b) by 760 days.

(21) Appl. No.: 12/649,378

(22) Filed: Dec. 30, 2009

(65) Prior Publication Data

US 2011/0160548 A1    Jun. 30, 2011

(51) Int. Cl.
*A61B 5/053* (2006.01)
*A61B 5/00* (2006.01)

(52) U.S. Cl.
CPC ............ *A61B 5/0002* (2013.01); *A61B 5/445* (2013.01); *A61B 2562/08* (2013.01); *A61B 5/053* (2013.01); *A61B 2560/045* (2013.01); *A61B 5/6833* (2013.01)
USPC ............ 600/386; 600/382; 600/393; 600/547

(58) Field of Classification Search
CPC .... A61B 5/053; A61B 5/0531; A61B 5/0537; A61B 5/445; A61B 2019/448; A61B 2562/08; A61B 19/44
USPC ................. 600/372, 382, 386, 393, 301, 547; 439/909
See application file for complete search history.

(56) References Cited

U.S. PATENT DOCUMENTS

| | | | |
|---|---|---|---|
| 7,015,826 B1 * | 3/2006 | Chan et al. ............... | 340/870.17 |
| 7,020,508 B2 * | 3/2006 | Stivoric et al. ................ | 600/390 |
| 7,048,687 B1 * | 5/2006 | Reuss et al. ................... | 600/300 |
| 7,170,415 B2 | 1/2007 | Forster | |
| 7,460,015 B2 | 12/2008 | Forster et al. | |
| 2003/0199783 A1 * | 10/2003 | Bloom et al. ................. | 600/549 |
| 2005/0245839 A1 * | 11/2005 | Stivoric et al. ............... | 600/549 |
| 2006/0052678 A1 * | 3/2006 | Drinan et al. ................ | 600/301 |
| 2006/0211936 A1 * | 9/2006 | Hu et al. ....................... | 600/386 |
| 2006/0264730 A1 * | 11/2006 | Stivoric et al. ............... | 600/390 |
| 2006/0270942 A1 * | 11/2006 | McAdams .................... | 600/547 |
| 2007/0276270 A1 * | 11/2007 | Tran .............................. | 600/508 |
| 2008/0076974 A1 * | 3/2008 | Yamazaki et al. ............ | 600/300 |
| 2008/0275327 A1 * | 11/2008 | Faarbaek et al. ............. | 600/382 |
| 2008/0319280 A1 * | 12/2008 | August et al. ................ | 600/301 |
| 2009/0184824 A1 | 7/2009 | Forster | |
| 2009/0264792 A1 * | 10/2009 | Mazar ........................... | 600/547 |
| 2011/0218418 A1 * | 9/2011 | Green et al. .................. | 600/386 |

* cited by examiner

*Primary Examiner* — Lee S Cohen
*Assistant Examiner* — Erin M Cardinal
(74) *Attorney, Agent, or Firm* — Avery Dennison Corporation

(57) ABSTRACT

A system for monitoring a physiological parameter comprises a substrate, a pair of drive electrodes, a pair of detection electrodes, and an RFID apparatus. The substrate is arranged to be removably securable to a biological organism. At least the pair of drive electrodes or the pair of detection electrodes is secured to the substrate. The RFID apparatus is arranged to be in electrical communication with at least the pair of drive electrodes or the pair of detection electrodes. Methods of using the device are also provided.

11 Claims, 5 Drawing Sheets

APPARATUS AND METHOD FOR MONITORING PHYSIOLOGICAL
PARAMETERS USING ELECTRICAL
MEASUREMENTS

TECHNICAL FIELD OF THE INVENTION

The present invention relates generally to monitoring physiological parameters and more particularly to monitoring physiological parameters using electrical measurements derived from voltage profiles obtained via radio frequency.

BACKGROUND OF THE INVENTION

Observing and evaluating the physiological condition of a biological subject, such as a human, may facilitate an evaluation of the health or wellness of the human or biological subject. For example, a medical professional may observe one or more physiological parameters of a patient to assist in determining the patient's overall health or wellness. Once the health and wellness of the patient is determined, the medical professional can advise the patient of any course of medical treatment that could improve the health and wellness of the patient.

Medical professionals often directly observe the physiological condition of a patient by visually inspecting or tactilely inspecting the patient's body. Such inspections generally lead to subjective assessments of a patient's physiological condition and thus a subjective assessment of the patient's health and wellness. In one example, when a patient has sustained a burn, cut, abrasion, or other such wound to the patient's flesh or tissue, the wound may be periodically visually inspected by a medical professional or the patient in an effort to determine the rate and progress of the healing process. In order to conduct such periodic visual inspections, a bandage or other type of dressing that may cover the wound would be removed to expose the wound for visual inspection. Bacteria or other such harmful organisms can enter the wound during this exposure and can result in the wound becoming infected or sustaining other such harmful effects. In addition, the regular removal of the wound dressing may become irritating to the patient and can lead to additional soreness, tearing of the wound or other unacceptable conditions.

SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In accordance with one embodiment, a system for monitoring a physiological parameter comprises a substrate, a first drive electrode, a second drive electrode, a first detection electrode, a second detection electrode, and a radio frequency identification ("RFID") device or apparatus. The substrate is arranged to be removably securable to a biological organism, such as through adhesive, mechanical fastening (e.g. incorporation in a wrap) or other suitable manners for securing the device to the patient. The first drive electrode, the second drive electrode, the first detection electrode, the second detection electrode, and the RFID apparatus are each coupled to the substrate. The RFID apparatus is arranged to be in electrical communication with each of the first drive electrode, the second drive electrode, the first detection electrode, and the second detection electrode.

RFID is a term used for technologies that use radio waves in the automatic identification of objects. There are several conventional methods of identifying objects using RFID, the most common of which is to store a serial number (and other information, if desired) that identifies a product on a microchip that is attached to an antenna. The chip and the antenna together along with the supporting substrate on which they are provided define an RFID inlay.

RFID devices include active tags and labels, which include a power source, and passive tags and labels, which do not. In the case of passive devices, in order to retrieve the information from the chip, a "base station" or "reader" sends an excitation signal to the RFID tag or label. The excitation signal energizes the tag or label, and the RFID circuitry transmits the stored information back to the reader. The RFID reader receives and decodes the information from the RFID tag. In general, RFID devices can retain and transmit enough information to uniquely identify individuals, packages, inventory and the like. RFID tags and labels also can be characterized as to those to which information is written only once (although the information may be read repeatedly), and those to which information may be written during use. For example, RFID devices may store environmental data (that may be detected by an associated sensor), logistical histories, state data, etc.

RFID devices or tags are used in a wide range of application environments. A typical RFID tag can include an RFID inlay having a circuit device, (hereinafter, "RFID inlay") that is mounted on a substrate or carrier, to which can be applied a facestock.

In accordance with another embodiment, a system for monitoring a physiological parameter comprises a patch, a first drive electrode, a second drive electrode, a first detection electrode, a second detection electrode, an RFID apparatus, and an RFID transceiver. The patch is arranged to be removably securable to a biological organism. The first drive electrode is coupled to the patch. The second drive electrode is coupled to the patch and located proximate, possibly adjacent, to the first drive electrode. The first detection electrode is coupled to the patch. The second detection electrode is coupled to the patch and located proximate to the first detection electrode. The RFID apparatus is coupled to the patch. The RFID apparatus is arranged to be in electrical communication with each of the first drive electrode, the second drive electrode, the first detection electrode, and the second detection electrode. The RFID transceiver is arranged to transmit radio signals to, and receive radio signals from, the RFID apparatus.

In accordance with another embodiment, a system for monitoring a physiological parameter comprises a first substrate, a second substrate, a first drive electrode, a second drive electrode, a first detection electrode, a second detection electrode, and an RFID apparatus. The first substrate and the second substrate are each arranged to be removably securable to a biological organism. The first drive electrode and the second drive electrode are coupled to the first substrate. The first detection electrode and the second detection electrode are coupled to the second substrate. The RFID apparatus is arranged to be in electrical communication with each of the first drive electrode, the second drive electrode, the first detection electrode, and the second detection electrode.

In accordance with another embodiment, a method is provided for monitoring a physiological parameter of a biological organism. The method comprises positioning an RFID apparatus proximate or adjacent to the biological organism. The method further comprises using the RFID apparatus to generate an electrical current in response to a signal request. The method further comprises quantifying characteristics of the electrical current. The method further comprises driving the electrical current through a portion of the biological organism. The method further comprises detecting a voltage from a voltage profile that has been radiated from the electrical current after it is driven through the portion of the biological organism. The method further comprises quantifying characteristics of the detected voltage to ascertain data or other parameters from the voltage.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

Figure 1:
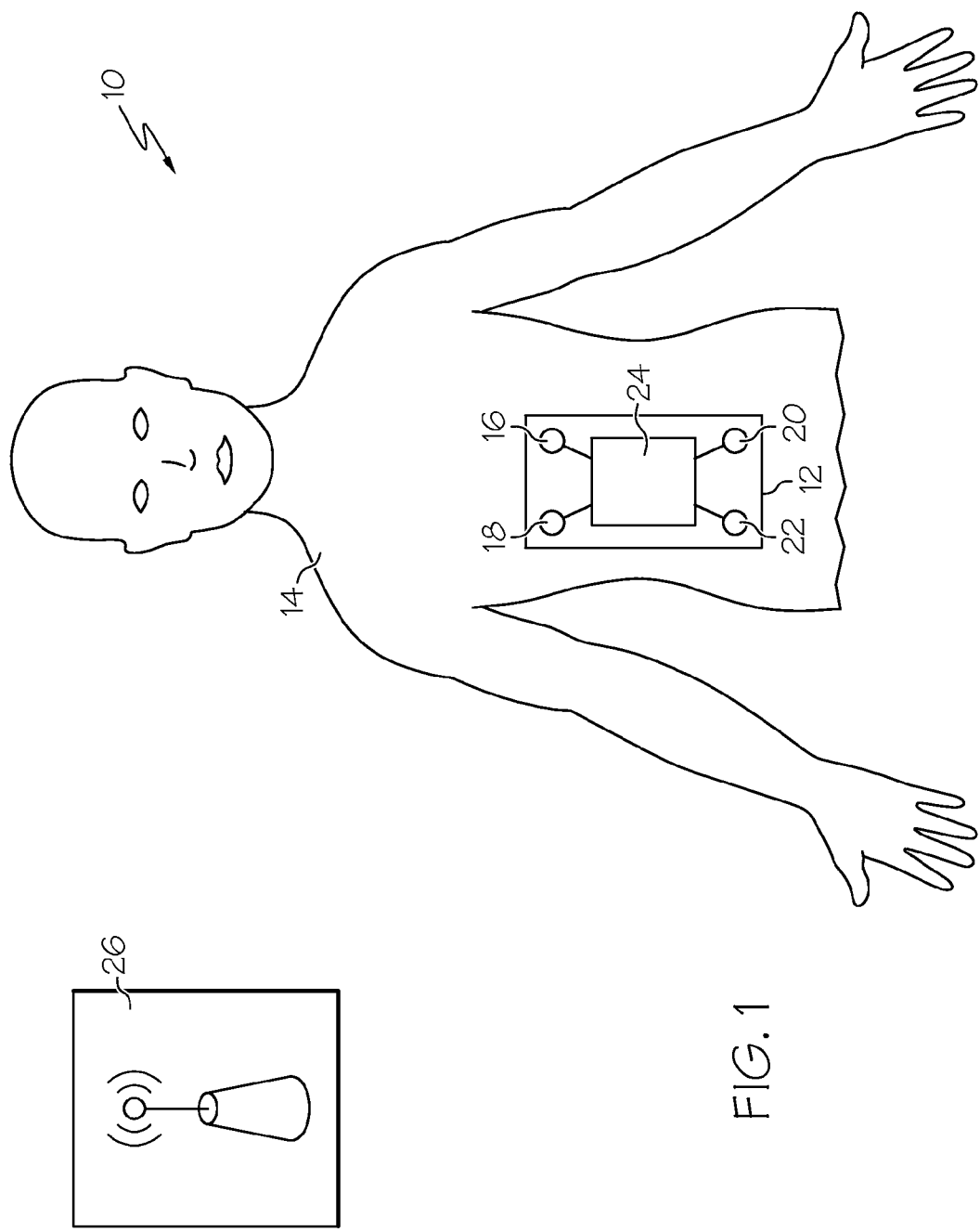
FIG. 1 is a schematic view depicting a system for monitoring physiological parameters in accordance with an embodiment, wherein a patch is removably secured to a human.

The apparatuses and methods disclosed in this document are described in detail by way of examples and with reference to the figures. Unless otherwise specified, like numbers in the figures indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be, and should not be, construed as mandatory or limiting unless specifically designated as such. Selected examples of apparatuses and methods for physiological monitoring of a biological organism using electrical measurements are hereinafter disclosed and described in detail with reference made to FIGS. 1 to 3.

Physiological monitoring can include the monitoring of at least one physiological parameter of a biological organism, such as a human. Physiological parameters of humans can include, for example, heart rate, respiration rate, body temperature, perspiration rate, the presence or level of bacteria, body hydration, and blood oxygen levels, among others. Physiological monitoring of a human or other biological organism can be useful for a number of purposes. For example, physiological monitoring can assist a doctor or other medical professional in assessing the health and wellness of a patient or diagnosing a disease, physical state or condition. By monitoring physiological parameters of interest to a medical professional who is treating the patient, the medical professional can recommend or initiate a course of medical treatment appropriate to address the patient's health, disease or condition.

An example of a method for monitoring at least one physiological parameter of a human includes measuring an electrical property of at least a portion of the human body. For example, such a method can include driving or providing an electrical current into a first portion of the human body. The properties or characteristics of the electrical current at the first portion of the human body can be controlled and thus determined and known. As a result of the driven electrical current, a voltage profile is established and can extend to a second portion of the human body, which is spaced from the first portion of the human body. This voltage profile can be measured and thus determined and known. Certain physiological parameters of the human body will cause a change in the characteristics of the voltage profile as it passes through the body, for example conductivity and dielectric constant. Therefore, by evaluating the characteristics of the voltage profile at the second portion of the human body, a physiological parameter of the skin or tissue positioned between the first and second portions of the human body can be determined. Determining such a physiological parameter can assist a medical professional in evaluating the health or condition of the human. By repeating this procedure over an extended period of time, a medical professional or a patient can monitor improvements or deteriorations of a human's health, condition or wellness.

An example of a physiological monitoring system 10 is schematically illustrated in FIG. 1. The physiological monitoring system 10 can include a substrate or patch 12 arranged to be removably securable to a body 14 of a human. The physiological monitoring system 10 can further include a pair of drive electrodes or contacts 16, 18, a pair of detection electrodes or contacts 20, 22, a radio frequency identification ("RFID") apparatus 24, and an RFID transceiver 26. The pair of drive electrodes 16, 18, the pair of detection electrodes 20, 22, and the RFID apparatus 24 can be coupled to the patch 12. The RFID transceiver 26 can be positioned a distance away from the patch 12 and arranged to provide for radio communication between the RFID transceiver 26 and the RFID apparatus 24.

The substrate or patch 12 may include an RFID device mounted directly to the substrate or the RFID device may be provided as a RFID inlay that is then applied to the patch. In either case, the substrate or inlay is selected from a material such as a polyester (e.g. PET), medical webbing, cellulosic stock (paper) or the like that generally will not react with the skin of the patient. The RFID device or inlay can be attached to the patient directly or to the substrate or patch 12 through the use of adhesives (e.g. permanent, removable, repositionable), cling films, mechanical fasteners such as clamps or clips or be bound to the patient as part of the dressing.

If the RFID device or inlay is provided or encoded with patient information, separation of the RFID inlay or RFID device from the substrate can cause a change in the read range or performance of the RFID device so as to protect the patient's privacy as may be required under certain statutory regulations. In this regard see US 2009/0184824 and U.S. Pat. No. 7,170,415. Alternatively, the RFID device can be provided with a destructible feature such as provided in U.S. Pat. No. 7,460,015, all of which have a common inventor and assigned to the same assignee as the present application, and each of which is hereby incorporated by reference herein as is necessary for a complete understanding of the present invention.

The drive electrodes 16, 18 can be arranged so that, when the patch 12 is secured to the body 14 of a human, the drive electrodes 16, 18 are in electrical communication with the skin or tissue of the body 14. Similarly, the detection electrodes 20, 22 can be arranged so that, when the patch 12 is secured to the body 14 of a human, the detection electrodes 20, 22 are in electrical communication with the skin or tissue of the body 14. In one embodiment, conductive adhesive can be placed on the patch 12, the drive electrodes 16, 18, and/or the detection electrodes 20, 22. In other embodiments, tape and/or some other material or arrangement can be used to facilitate securement of the patch 12 and associated components to the body 14. In one embodiment, it will be appreciated that the drive electrodes 16, 18 and/or the detection electrodes 20, 22 can contact the skin in a low resistance arrangement to facilitate effective transfer of electrical current therebetween. However, in another embodiment, it will be appreciated that elements can be coupled with a body in a capacitive or other configuration.

The RFID apparatus 24 can be positioned in electrical communication with each of the pair of drive electrodes 16, 18 and with each of the pair of detection electrodes 20, 22. The RFID transceiver 26 can be positioned and configured to send radio signals to, and receive radio signals from, the RFID apparatus 24. Likewise, the RFID apparatus 24 can be positioned and configured to send radio signals to, and receive radio signals from, the RFID transceiver 26.

Figure 2:
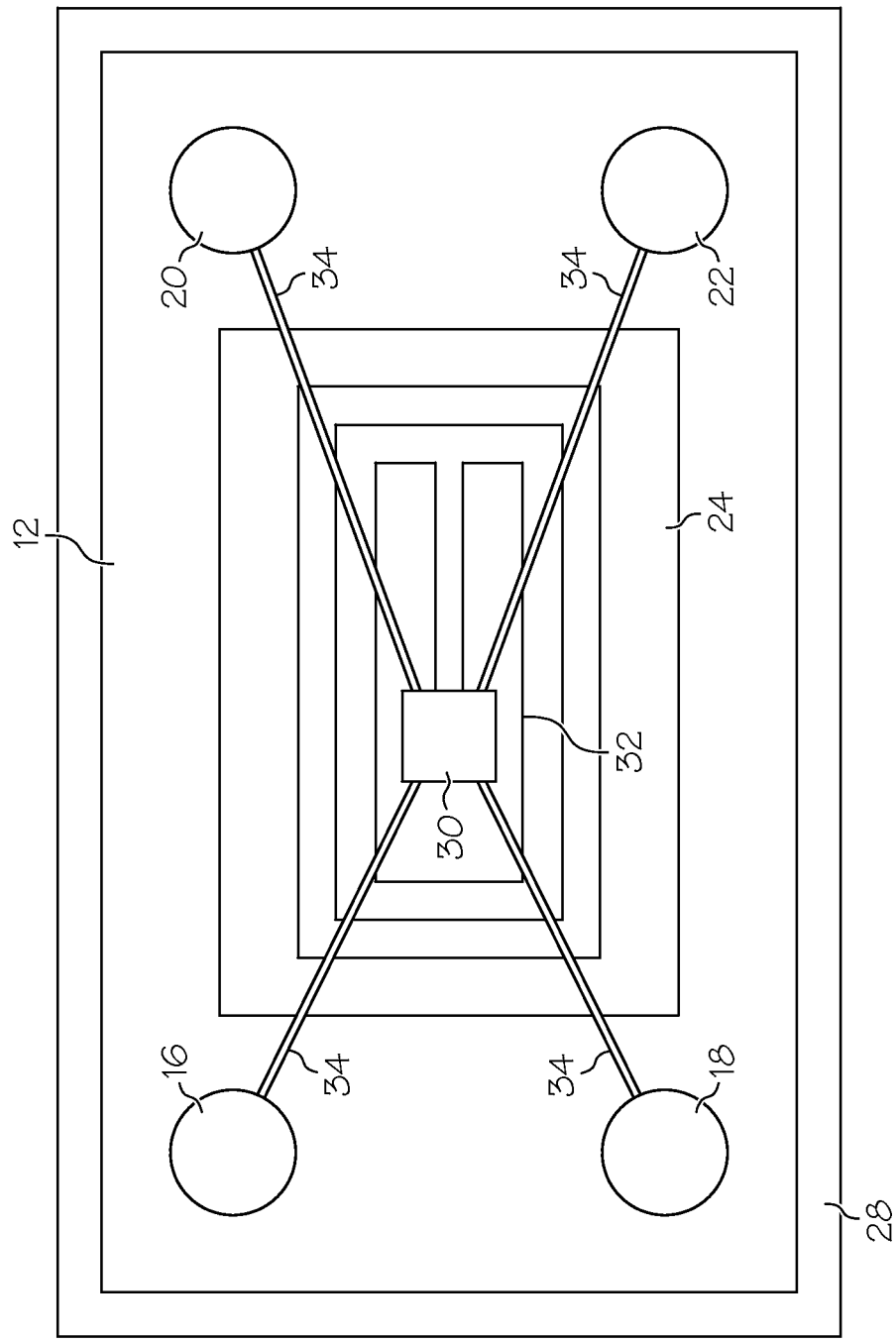
FIG. 2 is a schematic view depicting the patch of FIG. 1.

An example of the patch 12 with components coupled to the patch 12 is schematically illustrated in FIG. 2. The components as previously discussed can be provided as a RFID inlay which is then secured to or incorporated with the patch 12. The patch 12 can include an adhesive portion 28 for removably securing the patch 12 to the body 14 of a human or other biological subject. It will be understood that the adhesive portion 28 may include a generally tacky substance. The tacky substance can provide sufficient adhesive strength to secure the patch 12 to the body 14 of a human, but can allow for removal of the patch 12 from the body 14 of a human when desired. The drive electrodes 16, 18 can be coupled to the patch 12 and positioned generally proximate to one another, as shown in FIG. 2. The detection electrodes 20, 22 can also be coupled to the patch 12 and positioned generally proximate to one another and opposite the drive electrodes 16, 18, as also shown in FIG. 2. The RFID apparatus 24 is shown to be coupled to the patch 12 and positioned generally between the drive electrodes 16, 18 and the detection electrodes 20, 22. In other embodiments, an RFID apparatus can be positioned in any of a variety or suitable alternative locations relative to the drive electrodes and detection electrodes. Although the description and figures describe and illustrate a system with four electrodes, it will be understood that the system is not limited to four electrodes. A system can include either more than four or less than four electrodes.

The RFID apparatus 24 can include an RFID chip 30 and an antenna 32. In one embodiment, the RFID chip 30 can have a unique identifier to facilitate communication with the RFID transceiver 26 or other such device. The antenna 32 can be arranged so that it is in electrical communication with the RFID chip 30. The RFID device 24 can operate in any frequency range required, including low frequency (LF), high frequency (HF) or ultra high frequency (UHF). The antenna 32 can further be arranged to receive signals from devices such as the RFID transceiver 26 and arranged to transmit signals from the RFID chip 30. In generating a signal, the RFID chip 30 can encode the signal with data and other such information that can be read or otherwise interpreted by devices such as the RFID transceiver 26.

The RFID apparatus 24 can be in electrical communication with other components coupled to the patch 12. In one embodiment, as shown in FIG. 2, electrical leads 34, such as metal wires, place the RFID apparatus 24 in electrical communication with the drive electrodes 16, 18 and the detection electrodes 20, 22. In one example, as shown in FIG. 2, for each one of the drive electrodes 16, 18 and for each one of the detection electrodes 20, 22, a respective one of the electrical leads 34 can be provided to facilitate electrical communication with the RFID chip 30.

FIG. 2 illustrates the drive electrodes 16, 18, the detection electrodes 20, 22, and the RFID apparatus 24 as all coupled to the same side of the patch 12. However, it will be understood that electrodes and an RFID apparatus can be positioned in a variety or other suitable arrangements with respect to a patch. For example, electrodes can be coupled to one side of a patch while an RFID apparatus can be coupled to the opposing side of the patch. In yet another example, electrodes can be coupled to one side of a patch while an RFID apparatus is positioned and enclosed within a body of the patch. In another example, electrodes can be coupled to one side of a patch while an RFID apparatus is not coupled to the patch at all. The RFID components can be partially provided in an inlay, for example a chip connected to a small antenna could be provided in an inlay and then coupled to a larger antenna in the patch thereby making removal of the chip containing patient information easier and not requiring removal of the entire patch. In such examples, an RFID apparatus can still be arranged to be in electrical communication with the electrodes such as through use of electrical leads.

When the drive electrodes 16, 18 and the detection electrodes 20, 22 are coupled to the patch 12, and the patch 12 is secured to the body 14 of a human, a first voltage can be applied to the drive electrode 16 and a second voltage can be applied to the drive electrode 18, thereby creating a voltage differential between drive electrodes 16, 18. Because biological material, such as human skin and tissue, is generally conductive material, the human skin or tissue in contact with and/or in proximity to the drive electrodes 16, 18 can form a circuit through which an electrical current can flow. Therefore, the voltage differential between the drive electrodes 16, 18 can result in electrical current being driven through the skin or tissue that is positioned between the drive electrodes 16, 18. In one embodiment, a relatively low differential voltage can result in driving this electrical current through the skin or tissue.

As a result of the electrical current passing through the skin or tissue between the drive electrodes 16, 18, a voltage profile is established throughout the tissue surrounding the path of the electrical current, including through tissue located between the drive electrodes 16, 18 and the detection electrodes 20, 22. The voltage profile reaches the detection electrodes 20, 22, and a voltage can be detected at the detection electrodes 20, 22. The magnitude of the voltage present at the detection electrodes 20, 22 can depend both upon the characteristics of the electrical current driven by the drive electrodes 16, 18 and upon the conditions of the skin and tissue disposed between the drive electrodes 16, 18 and the detection electrodes 20, 22. As will be subsequently described, by assessing the voltages measured at the detection electrodes 20, 22 in light of the electrical current driven by the drive electrodes 16, 18, physiological parameters of the skin or tissue located between the drive electrodes 16, 18 and the detection electrodes 20, 22 can be determined and those parameters compared with a set of standard parameters to obtain a reading on the particular condition being monitored.

In one embodiment, the electrical current applied by the drive electrodes 16, 18 is an alternating electrical current ("AC current"). AC current, as used herein, shall not be limited to AC current having a true sinusoidal waveform, but shall also include AC current waveforms having a simulated sinusoidal waveform including, for example, those generated through pulse width modulation. In another embodiment, a direct current can be used. It will also be alternatively understood that other types of electric, magnetic or acoustic energy can be applied to skin and tissue to facilitate assessment of physiological parameters of a biological subject.

The RFID apparatus 24 can be arranged to generate and control the electrical current propagated through the biological subject and between the drive electrodes 16, 18. For example, the RFID chip 30 can be arranged to vary the differential voltage provided across the drive electrodes 16, 18, and resultingly vary the magnitude and/or other characteristics of the electrical current propagated through the biological subject between the drive electrodes 16, 18. The RFID chip 30 can additionally or alternatively be configured to vary the waveform, pulse, and/or frequency of the electrical current imposed upon the biological subject.

The RFID apparatus 24 can be arranged to receive and direct energy in any of a variety of suitable configurations. In one embodiment, the RFID apparatus 24 (a passive tag) can receive radio signals transmitted by the RFID transceiver 26 and transform a portion of the energy of the received radio signals into electrical energy for selectively providing to the drive electrodes 16, 18. In another embodiment, the RFID apparatus 24 can include an onboard power source (an active tag), such as a battery or capacitor, from which electrical energy can be retrieved and directed to the drive electrodes 16, 18.

As the electrical current propagates through tissue located between the drive electrodes 16, 18, a voltage profile can be detected (e.g., as a voltage) at the detection electrodes 20, 22. The voltage profile detected at the detection electrodes 20, 22 can then be evaluated. For example, if a voltage is detected, the amplitude, waveform, phase, and/or frequency can be measured, read, or otherwise determined. Comparing these characteristics to the known or a standardized set of characteristics of the electrical current introduced in the biological subject by the drive electrodes 16, 18 can result in a determination of physiological parameters of the skin or tissue located between the drive electrodes 16, 18 and the detection electrodes 20, 22 so that the healthcare professional can determine the current condition or status of the patient being treated.

In one embodiment, the RFID apparatus 24 includes logic or embedded instructions to facilitate the operations needed to determine or monitor a physiological parameter as described above. The RFID apparatus 24 can include onboard memory to store logic or instructions to execute operations such as directing energy to the drive electrodes 16, 18; determining or quantifying properties or characteristics of the electrical current applied to the tissue between the drive electrodes 16, 18; detecting voltages at the detection electrodes 20, 22; determining or quantifying properties or characteristics of the voltage profile detected by the detection electrodes 20, 22; comparing the characteristics of the electrical current propagated between the drive electrodes 16, 18 and the characteristics of the voltage profile detected by the detection electrodes 20, 22; and determining or quantifying a physiological parameter based on the comparison. In addition, the RFID apparatus 24 can store data regarding determinations and quantifications in such onboard memory.

In another embodiment, the RFID apparatus 24 receives signals from the RFID transceiver 26 encoded with instructions to execute the operations detailed above. In such an embodiment, the RFID transceiver 26 can include onboard memory to store the logic or instructions to execute such operation and can transmit such instructions to the RFID apparatus 24 for execution. In addition, the RFID apparatus 24 can transmit signals encoded with data back to the RFID transceiver 26 for storage within the memory of the RFID transceiver 26. In other embodiments, the RFID transceiver 26 can be arranged to communicate with a computing device or alternatively be incorporated into a computing device. Such a computing device can be configured to evaluate, compare, and/or store electrical measurements taken of the biological subject. The computing device can further be configured to inform medical professionals of the results of the evaluation of the electrical measurements and/or warn medical professionals of conditions that require medical attention.

When the electrical current propagated between the drive electrodes 16, 18 is an AC current, the frequency of the AC current can be varied to assist is facilitating the determination of the desired physiological parameter. In one embodiment, the frequency can be derived from a clock frequency sent by the RFID transceiver 26 to the RFID chip 30. In another embodiment, the RFID apparatus 24 can include an onboard clock from which the drive frequency is derived. In one embodiment, the frequency of the AC current can be kept relatively low. In such an embodiment, flow of the voltage profile due to the AC current is distributed relatively evenly throughout the tissue positioned between the drive electrodes 16, 18 and the detection electrodes 20, 22. However, as frequency of the AC current is increased, the flow of the energy can begin to concentrate near the surface of the tissue at the skin layer. Therefore, if it is desired that a physiological parameter near the surface of the tissue or skin is to be measured, a higher frequency can be appropriate. If it is desired that a physiological parameter that is located deeper in the tissue is to be measured, a lower frequency can be appropriate. In addition to varying frequency, any of a variety of other parameters (e.g., magnitude, waveform, and phase) of the induced electrical current can be varied to facilitate determination of a physiological parameter.

In one embodiment, a patch 12 is placed over an open and relatively deep wound on the body 14 of a person. When the wound is recent, both relatively low frequencies and relatively high frequencies can be used to evaluate the wound. For example, an AC current with a relatively high frequency can be used to evaluate the wound near the surface of the body, while an AC current with a relatively low frequency can be used to evaluate the wound deeper into the tissue. Various physiological parameters can affect the voltages detected by the detection electrodes 20, 22. For example, healed tissue will affect the detected voltages differently than damaged tissue. Therefore, by applying AC currents of varying frequency, the depth of the wound can be determined. Over time, the rate and progress of the healing deep in the wound can be determined by comparing readings over a period of days or weeks and at different depths of the wound. In another example, relatively high frequency AC currents can be used to inspect the surface of the wound to determine physiological parameters (e.g., level of bacteria present in the wound and the level of clotting at the surface of the wound) without removing the patch 12.

In another embodiment, a patch 12 is secured to a patient on healthy skin. An AC current is propagated between the drive electrodes 16, 18 and voltages are detected by the detection electrodes 20, 22. The level of hydration of the patient at least in part determines the characteristics and values of the driven AC current and voltages detected by the detection electrodes 20, 22. Therefore, by comparing the characteristics of the induced current and measured voltages, the hydration level of the patient can be determined. By taking periodic readings and making comparisons, the patient's hydration level can be monitored over time. If it is determined that the patient is dehydrated, a medical professional can take proactive steps to hydrate the patient.

Figure 3:
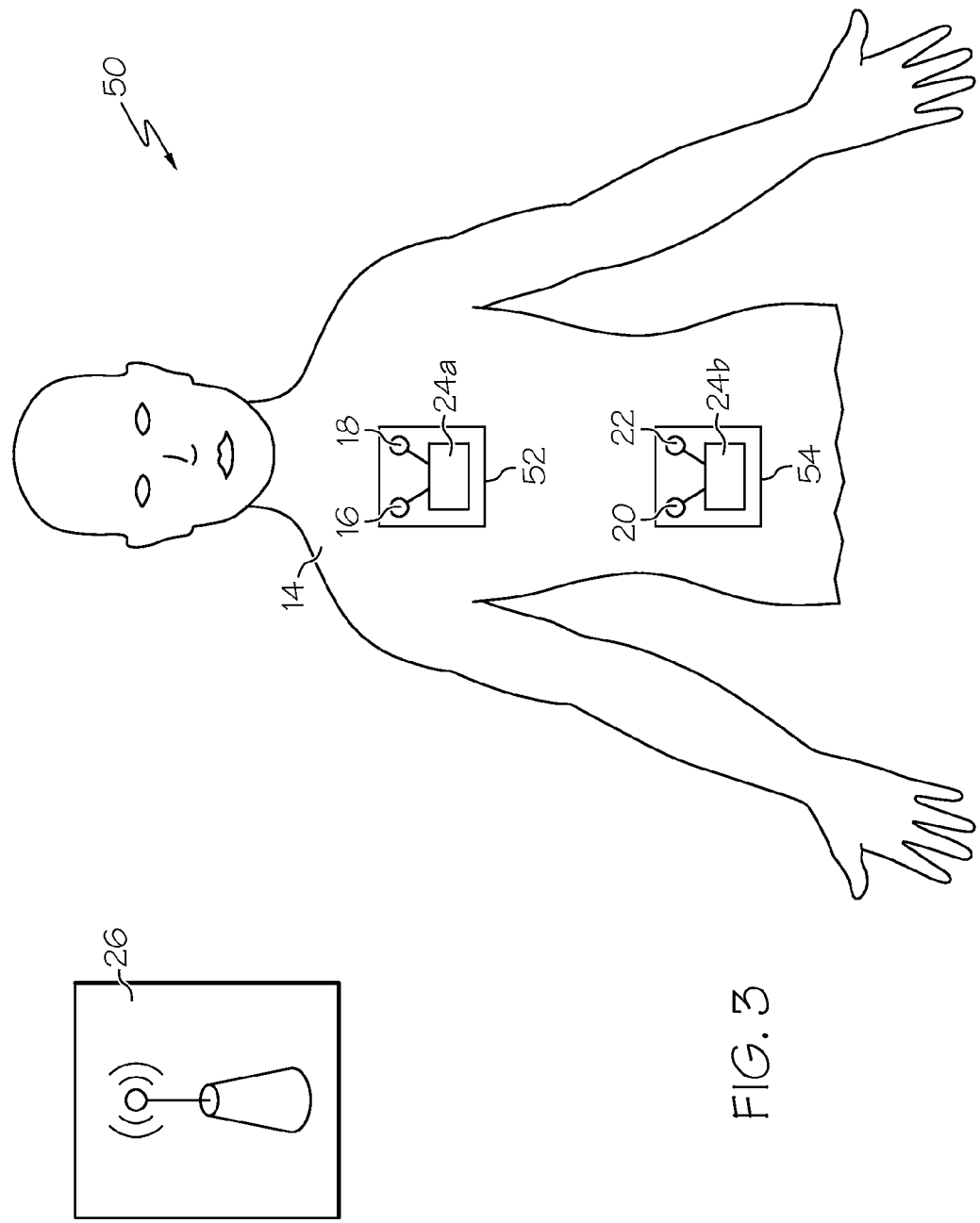
FIG. 3 is a schematic view depicting a system for monitoring physiological parameters in accordance with another embodiment, wherein two patches are removably secured to a human.

Another embodiment of a physiological monitoring system 50 is schematically illustrated in FIG. 3. The physiological monitoring system 50 can include a drive patch 52 and a detection patch 54. The drive patch 52 can include drive electrodes 16, 18 and an RFID apparatus 24a. The detection patch 54 can include detection electrodes 20, 22 and an RFID apparatus 24b. In such an embodiment, the functionality to drive the electrical current and the functionality to detect voltages are divided among the drive and detection patches 52, 54. Therefore, the drive patch 52 and the detection patch 54 can be placed at varying distances from one another on the body 14 to allow for the determination of physiological parameters through large portions of the body 14. In one example, such an embodiment can be utilized to detect physiological parameters such as respiration rate.

The RFID apparatuses 24a, 24b can each have a unique identifier to facilitate communication between the RFID apparatuses 24a, 24b and the RFID transceiver 26. The RFID transceiver 26 can be arranged to send signals to the RFID apparatus 24a with instructions regarding appropriate operations for the drive patch 52. Such instructions can relate to, for example, directing energy to the drive electrodes 16, 18, and/or determining or quantifying properties or characteristics of the voltages and electrical current imposed on the body 14 between the drive electrodes 16, 18. Similarly, the RFID transceiver 26 can be arranged to send signals to the RFID apparatus 24b with instructions for appropriate operations for the detection patch 54. Such instructions can relate to, for example, detection of voltage and/or other properties or characteristics of the voltage profile received by the detection electrodes 20, 22, and instructions regarding the manner in which this information should be transmitted from the RFID apparatus 24b to the RFID transceiver 26. Upon receipt of data or information from one or both of the RFID apparatuses 24a, 24b, the RFID transceiver 26 can compare the drive electrical current and the detected voltage, and can determine or quantify a physiological parameter based on comparisons and/or can pass this information along to another device (e.g. a computer) to facilitate this determination or quantification.

Figure 4:
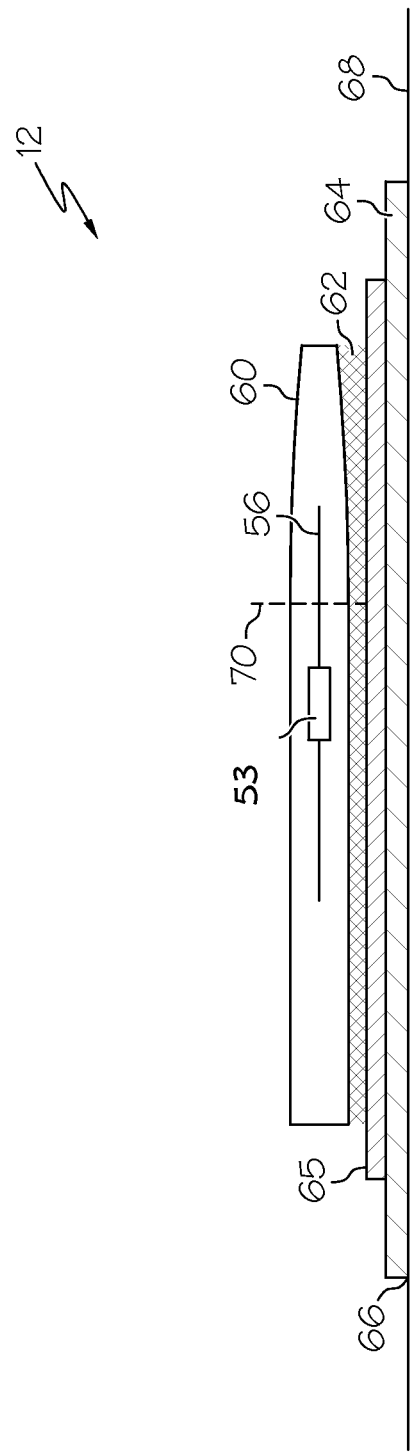
FIG. 4 provides a cross sectional view of the patch of FIG. 1.

Reference is now directed to FIG. 4 which provides a cross sectional elevation of the patch 12 to illustrate further exemplary embodiments of the invention. An inlay 60 that contains a chip 53 and at least a portion of an antenna 56 is adhesively attached by a pattern of adhesive 62 to a second substrate 64 which may then be adhesively applied by a layer of adhesive 66 to the patient 68. The second substrate 64 may contain a larger antenna 65 to which the inlay 60 may be coupled. Where the RFID device 12 is adhered or coupled directly to the surface 68, a destruct feature such as a line of weakness (perforation line) can be used to destroy a portion of the RFID device to thereby limit or reduce the read range of the device.

As indicated previously, in order to protect to the privacy of the patient, removal of the inlay 60 from the surface 68 can be done in such a manner that the performance of the RFID device is reduced or operational parameters are changed.

Figure 5:
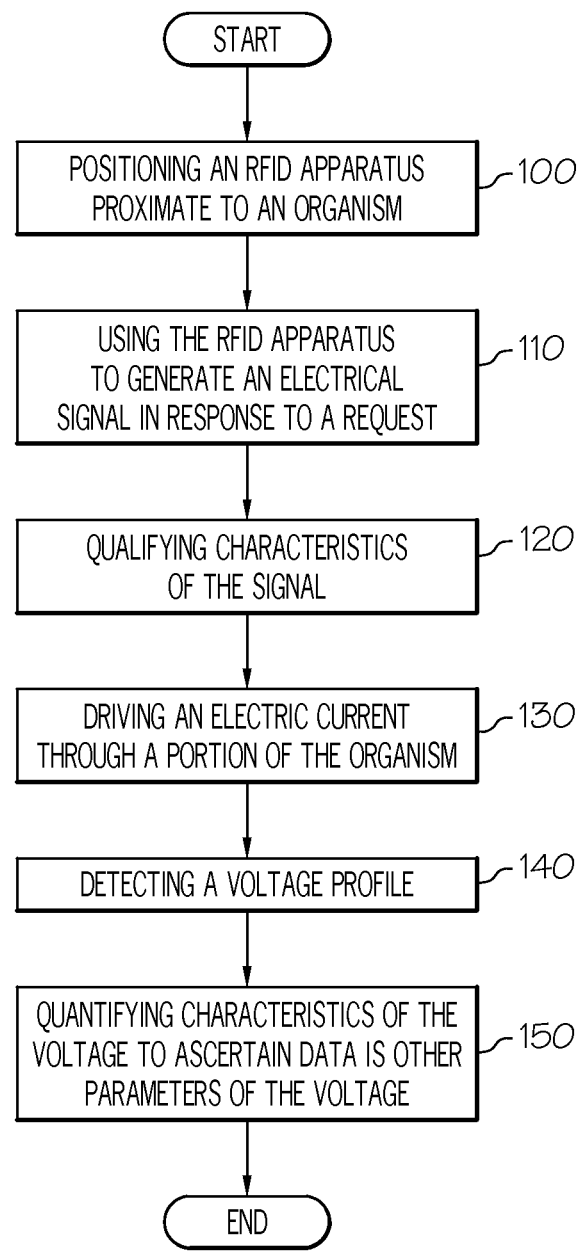
FIG. 5 depicts a block diagram of an exemplary method of using the patch of the present invention.

Reference is now directed to FIG. 5 which is a block diagram illustrating exemplary steps in practicing the present invention. The process is started and at step 100 an RFID apparatus or device is positioned near or proximate to a biological organism, such as positioning the RFID device on the skin of a patient. Next, at step 110, the RFID device is used to generate an electrical signal in response to a request. At step 120, the characteristics of the signal are quantified. The electric current is driven through a portion of the organism at step 130. A voltage profile is detected at step 140 and the characteristics of the voltage profile are quantified at step 150 to ascertain data or other parameters of the voltage profile.

The signal that is generated can penetrate the organism at different depths which will result in several voltage profiles being returned, with each profile indicative of a particular condition at the level where the voltage is received.

The foregoing description of examples has been presented for purposes of illustration and description. It is not intended to be exhaustive or limiting to the forms described. Numerous modifications are possible in light of the above teachings. Some of those modifications have been discussed, and others will be understood by those skilled in the art. The examples were chosen and described in order to best illustrate principles of various examples as are suited to particular uses contemplated. The scope is, of course, not limited to the examples set forth herein, but can be employed in any number of applications and equivalent devices by those of ordinary skill in the art.

What is claimed is:

1. A system for monitoring a physiological parameter comprising:
   a substrate arranged to be removably securable to a biological organism;
   a first drive electrode, a second drive electrode, a first detection electrode, a second detection electrode, and an RFID device having a chip with a unique identifier, each disposed on the substrate;
   an RFID transceiver; and
   wherein the RFID device is in electrical communication with each of the first drive electrode, the second drive electrode, the first detection electrode, and the second detection electrode,
   wherein the RFID device is configured to provide an electrical signal to each of the first and second drive electrodes and the RFID device is configured to detect a voltage at each of the first and second detection electrodes,
   wherein the RFID device is configured to determine a voltage profile based at least in part on the voltages detected at the first and second detection electrodes, and
   wherein the RFID device is configured to determine the physiological parameter, which is a wound depth, by applying AC currents of varying frequency, and wherein the RFID transceiver is arranged to transmit radio signals to, and receive radio signals from, the RFID device.

2. A system as recited in claim 1, wherein the RFID device further comprises:
   logic configured to determine an additional physiological parameter from the voltage profile; and
   the additional physiological parameter includes at least one of: heart rate, respiration rate, body temperature, perspiration rate, the presence or level of bacteria, body hydration, blood oxygen levels or combinations thereof.

3. A system as recited in claim 1, wherein the RFID device further includes a memory device.

4. A system as recited in claim 1, wherein the RFID device includes an on-board power supply.

5. A system as recited in claim 4, wherein the on-board power supply is a battery.

6. A system as recited in claim 1, wherein the RFID device is configured to determine the voltage profile at various wound depths.

7. A system as recited in claim 1, wherein the electrical signal provided to the first drive electrode comprises a first voltage and the electrical signal provided to the second drive electrode comprises a second voltage.

8. A system for monitoring a physiological parameter, comprising a patch, a first drive electrode, a second drive electrode, a first detection electrode, a second detection electrode, a passive RFID apparatus, and an RFID transceiver; wherein:
- the patch is arranged to be removably securable to a biological organism;
- the first drive electrode and the first detection electrode are each coupled to the patch;
- the second drive electrode is coupled to the patch and located proximate to the first drive electrode;
- the second detection electrode is coupled to the patch and located proximate to the first detection electrode;
- the first drive electrode, the second drive electrode, the first detection electrode, and the second detection electrode are coupled to the patch in a non-linear arrangement;
- the RFID apparatus is coupled to the patch;
- wherein the RFID apparatus is arranged to be in electrical communication with each of the first drive electrode, the second drive electrode, the first detection electrode, and the second detection electrode,
- wherein the RFID apparatus is configured to provide an electrical signal to each of the first and second drive electrodes and the RFID apparatus is configured to detect a voltage at each of the first and second detection electrodes;
- the RFID transceiver is arranged to transmit radio signals to, and receive radio signals from, the RFID apparatus and the RFID transceiver determines the physiological parameter from the received radio signals; and
- wherein the RFID apparatus is configured to determine a wound depth by applying AC currents of varying frequency.

9. The system as provided in claim 8, wherein the electrical signal provided to the first drive electrode comprises a first voltage and the electrical signal provided to the second drive electrode comprises second voltage.

10. The system as provided in claim 9, wherein the first and second voltages are configured to create a voltage profile configured for monitoring of the physiological parameter.

11. The system as provided in claim 8, wherein the RFID transceiver includes instructions to provide an additional electrical signal to evaluate the physiological parameter and the physiological parameter includes at least one of: heart rate, respiration rate, body temperature, perspiration rate, the presence or level of bacteria, body hydration, blood oxygen levels or combinations thereof.

* * * * *